United States Patent [19]

Ohta

[11] Patent Number: 4,883,668
[45] Date of Patent: Nov. 28, 1989

[54] MATERIAL FOR ENDERMIC ADMINISTRATION PRE-TREATMENT

[75] Inventor: Midori Ohta, Funabashi, Japan

[73] Assignee: Kabushiki Kaisya Advance, Tokyo, Japan

[21] Appl. No.: 309,892

[22] Filed: Feb. 15, 1989

Related U.S. Application Data

[63] Continuation of Ser. No. 144,034, filed as PCT JP87/00261 on Apr. 24, 1987, published as WO87/06477 on Nov. 5, 1987, abandoned.

[30] Foreign Application Priority Data

Apr. 24, 1986 [JP] Japan ................................. 61-93405

[51] Int. Cl.$^4$ ............................................. A61F 13/02
[52] U.S. Cl. ...................................... 424/448; 604/47
[58] Field of Search ............... 424/443, 448, 449, 484, 424/485, 486; 604/47

[56] References Cited

U.S. PATENT DOCUMENTS

| | | | |
|---|---|---|---|
| 3,339,546 | 9/1967 | Chen | 424/448 |
| 3,342,183 | 9/1967 | Edenbaum | 424/448 |
| 4,140,115 | 2/1979 | Schonfeld | 428/411.1 |
| 4,510,197 | 4/1985 | Shah | 428/220 |
| 4,588,762 | 5/1986 | Mruk et al. | 424/449 |
| 4,592,753 | 6/1986 | Panoz | 424/449 |
| 4,699,792 | 10/1987 | Nick et al. | 424/448 X |
| 4,714,655 | 12/1987 | Bordoloi et al. | 424/448 |

FOREIGN PATENT DOCUMENTS 57-123117 7/1982 Japan.
60-54284 11/1985 Japan.

OTHER PUBLICATIONS

J. M. Glass et al., Int. J. Dermatol., 19, 519 (1980).
J. Russo et al., Am. J. Hosp. Pharm., 37, 843 (1980).
L. P. Gangarosa et al., J. Pharmcol. Exp. Ther., 212, 377 (1980).
B. S. Kwon et al, J. Infect. Dis., 140, 1014 (1979).
J. J. Hill et al., Ann. NY. Acad. Sci., 284, 604 (1977).
M. Tannebaum, Phys. Ther., 60,792 (1980).

*Primary Examiner*—Thurman K. Page
*Attorney, Agent, or Firm*—Finnegan, Henderson, Farabow, Garrett, Dunner

[57] ABSTRACT

A material for endermic administration pre-treatment is disclosed wherein the material comprises a support and a substance capable of removing corneum, for example, an adhesive, and the substance is substantially uniformly distributed on the support in the form of small areas discontinuous to each other at a density of 0.001 to 5%. Pre-treatment of the skin by this material enhances the absorption of a medicament in an endermic administration.

11 Claims, 4 Drawing Sheets

MATERIAL FOR ENDERMIC ADMINISTRATION PRE-TREATMENT

DESCRIPTION

This application is a continuation of application Ser. No. 144,034, filed as PCT JP87/00261 on Apr. 24, 1987, published as WO87/06477 on Nov. 5, 1987, now abandoned.

TECHNICAL FIELD

The present invention relates to a material for an endermic administration pre-treatment, which material is pressed against the skin and removed therefrom prior to endermic administration, to produce fissures, for example, fine openings or microcracks, on the stratum corneum which forms a surface layer of the skin, to an extent such that no substantial irritation occurs.

BACKGROUND ART

The administration of a medicament through endermism is considered to be the best means of providing considerable pharmaceutical effects without causing side effects, i.e., gastrointestinal disorders which occur upon a peroral administration. Recently, an iontophoresis treatment, which enhances the absorption through endermism by an electric means, has attracted particular attention. Reference is made to, for example, J. M. Glass et al, Int. J. Dermatol., 19,519 (1980); J. Russo et al, Am. J. Hosp. Pharm., 37, 843 (1980); L. P. Gangarosa et al, J. Pharmacol. Exp. Ther., 212,377 (1980); B. S. Kwon et al, J. Infect. Dis., 140, 1014 (1979); J. M. Hill et al, Ann. N.Y. Acad. Sci., 284, 604 (1977); and M. Tannebaum, Phys. Ther., 60,792 (1980).

In endermism, which is a passive-diffusive system, the endermic absorbability of a pharmaceutically active component has not been sufficiently elucidated, and thus the selection of an effective medicament is made on the basis of experience, but there are few medicaments which can be employed for this purpose. Medicaments which can exhibit sufficient effects in iontophoresis are also limited.

It has been found that if a very few microcracks or fine openings are produced, on a stratum corneum of a skin at a portion to be treated through endermism, before carrying out a usual endermism operation, the physical and electrical resistances inherently shown by the skin tissue against the endermic absorption of the medicaments can be considerably reduced, and thus the endermism can be efficiently enhanced.

Accordingly, a first object of the present invention is to provide a material for endermic administration pre-treatment, which material can be pressed against the skin and removed therefrom to thereby produce microcracks or fine openings on the stratum corneum, substantially without pain or irritation.

Further, a second object of the present invention is to provide a method for endermic administration pre-treatment, wherein microcracks or fine openings are produced on the stratum corneum, substantially without pain or irritation.

DISCLOSURE OF THE INVENTION

The above first object can be achieved, in accordance with the present invention, by a material for endermic administration pre-treatment, characterized in that the material comprises a support and a substance capable of removing corneum, and said substance is substantially uniformly distributed on the support in the form of small areas, discontinuous to each other, at a density of 0.001 to 5%.

The above second object can be achieved, in accordance with the present invention, by a method for endermic administration pre-treatment, characterized in that a substance which is capable of removing corneum and substantially uniformly distributed on a support in the form of small areas, discontinuous to each other and at a density of 0.001 to 5%, is pressed against a skin to which endermic administration is to be applied, thereby adhering said substance to corneum on said skin, and thereafter, the substance together with the support is removed from the skin, thereby removing from the skin at least a portion of the corneum adhered to the substance.

BEST MODE FOR CARRYING OUT THE INVENTION

Figure 1:
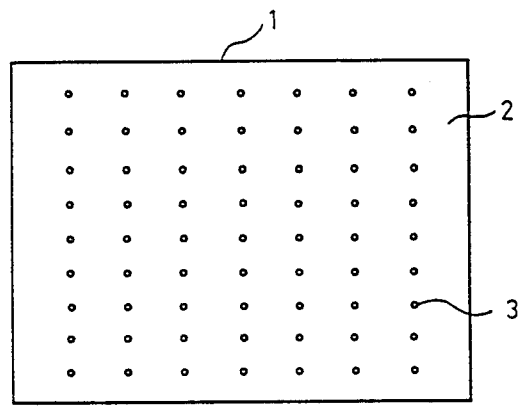
FIG. 1 is a plan view of one embodiment of the pre-treatment material according to the present invention.

The material for an endermic administration pre-treatment according to the present invention comprises the support and the substance capable of removing corneum.

As the support, any materials including a flexible material or a rigid material may be employed. The flexible materials which may be used are, for example, a plastic film, cellophane, cloth, paper or the like. Examples of the plastic film are films made of polyvinyl chloride, polyester, polyethylene or cellulose acetate. A laminated film formed from a combination thereof also may be used. The rigid materials which may be used are, for example, plastic or metallic plates.

The term "substance capable of removing corneum" as used herein means a substance which can adhere to a screloprotein, which is a constituent of the stratum corneum forming the surface layer of the human skin, and remove at least a portion of said screloprotein from the skin. The substance should be essentially harmless to the skin except for the removal of corneum, which is the purpose of the present invention.

Typical of the substances capable of removing corneum is an adhesive, particularly a pressure sensitive adhesive.

An adhesive strength of the pressure sensitive adhesive used in the present invention is generally 30 kgf/cm$^2$ or more, preferably 50 kgf/cm$^2$ or more, particularly 100 kgf/cm$^2$ or more.

The pressure sensitive adhesives which may be used in the present invention are, for example, rubber adhesives such as those containing natural rubber, regenerated rubber, or synthetic rubber such as isoprene rubber, styrene-butadiene rubber, nitrile-butadiene rubber, chloroprene rubber or butyl rubber; acrylic adhesives such as those containing mainly acrylate of aliphatic alcohol having 2 to 12 carbon atoms; water-based adhesives such as polyvinyl alcohol, isobutene-maleic anhydride copolymer, polyacrylamide, polyethylene oxide, polyvinyl pyrrolidone, vinyl acetate copolymer, acrylic copolymer, vinyl methyl ether-maleic anhydride copolymer; or polyvinyl ether, polyisobutyl ether or the like.

In the present invention, non-solvent based pressure sensitive adhesives also may be used. The non-solvent based pressure sensitive adhesives are, for example, emulsion based adhesives such as synthetic rubber latex, polyvinyl acetate based, vinyl acetate-ethylene copolymer based, polyacrylate based or polyvinyl chloride based adhesives; oligomer based adhesives such as rubber oligomer based, acrylic oligomer based or urethane oligomer based adhesives.

Further, curable type pressure sensitive adhesives also may be used. As the curble type adhesives, there may be mentioned, for example, a hygroscopic curable adhesive such as cyanoacrylate based adhesive; or an anaerobic curable adhesive such as tetraethylene glycol dimethacrylate.

Further, solvent-activating adhesives, for example, a water-activating adhesive such as glue, gum arabic, dextrin, polyvinyl alcohol, acrylics, polyacrylamide, polyethylene oxide or the like, and an organic solvent-activating adhesive also can be used.

Furthermore, capsular adhesives can be employed. When the capsular adhesive is used, any adhesive can be encapsulated in microcapsule several to tens of microns thick. Alternatively, a curing agent such as peroxide (e.g., hydrogen peroxide) can be encapsulated in microcapsule several to tens of microns thick, and dispersed in an adhesive such as acrylic monomer.

The pressure sensitive adhesive of the present invention can be classified in view of the chemical composition thereof, as follows: a natural adhesive such as a starch based adhesive (e.g., dextrin), protein based adhesive (e.g., glue) or natural rubber based adhesive; a thermoplastic adhesive such as a vinyl acetate, polyvinyl alcohol, vinyl chloride, acrylic compound, polyamide, polyethylene, cellulose, polyisobutylene or polyvinyl ether based adhesive; a synthetic rubber based adhesive such as a chloroprene, nitrile rubber, styrene rubber or butyl rubber based adhesive.

According to the present invention, the above substance capable of removing corneum is substantially uniformly distributed on the support in the form of small areas discontinuous to each other. The shape of the small area is not limited. For example, the area can be a circle about 10–300 μm in diameter (or an ellipse having a similar square measure), a strip about 10–300 μm in width (straight or curved), or any other shape. A combination of various shaped small areas may be formed on the support.

The small areas can be formed by applying the above substance capable of removing corneum on the support by a conventional printing technique, spraying technique or the like.

The density of the small areas is 0.001–5%, preferably 0.01–1%. The term "density of the small areas" means a ratio of effectively active portions in the above substance forming the small areas to the support surface pressed against the skin. When the density of the small areas is less than 0.001%, the sheet of the present invention does not achieve the required purpose. When the density is above 5%, disadvantages such as erythrochromia or irritation occur.

The pre-treatment material according to the present invention is, for example, a sheet such as a tape (including a roll) or a label, and is used by appropriately selecting the size or shape thereof in accordance with the site to which it is to be applied. Further, the pre-treatment material according to the present invention also may be a relatively thick plate. Particularly, when the rigid pre-treatment plate is used, preferably, for the pre-treatment, a handle is provided which can be grasped by hand, on the surface opposite to the surface carrying the substance capable of removing corneum. The pre-treatment material according to the present invention can carry a protective film layer on the surface having the substance capable of removing corneum to avoid drying of said substance prior to use.

The pre-treatment material according to the present invention can be employed before carrying out the endermic administration. The endermic administration is carried out, for example, by putting a plaster on the skin or by iontophoresis.

The present invention now will be illustrated by, but is by no means limited to, the following Examples.

EXAMPLES

Manufacturing Example 1

On a surface of a polyvinyl chloride film (10 cm × 10 cm3 × mm), dotting pits (diameter about 100 μm and depth about 50 μm) were dug uniformly at a ratio of 200 pits/cm$^2$. An adhesive based on an emulsion of vinyl acetate ethylene was poured into the pits to obtain the pre-treatment sheet according to the present invention (adhesive density: 1.5%).

Figure 2:
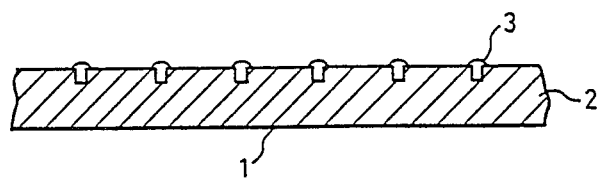
FIG. 2 is a sectional view on an enlarged scale of a portion of the material of FIG. 1.

As shown in FIG. 1, the pre-treatment sheet 1 produced in this Example uses an adhesive 3, based on an emulsion of vinyl acetate ethylene, on the polyvinyl chloride film 2. FIG. 2 is an enlarged sectional view of a part of the above sheet.

Manufacturing Example 2

On a surface of a polyvinyl chloride film, as in the above Manufacturing Example 1, a cyanoacrylate based adhesive was applied uniformly in the form of dots (diameter: about 80 μm) at a ratio of 200 dots/cm$^2$ to obtain the pre-treatment material of the present invention (adhesive density: 1.0%).

Figure 3:
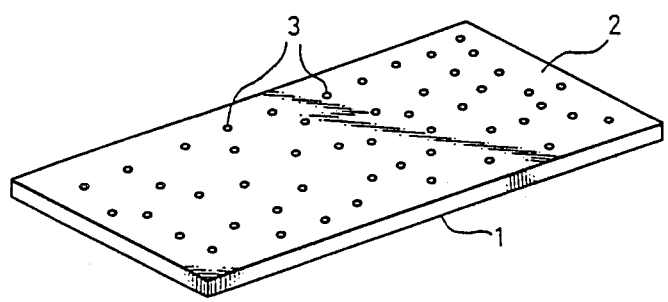
FIG. 3 is a plan view of another embodiment of the pre-treatment material according to the present invention.
Figure 4:
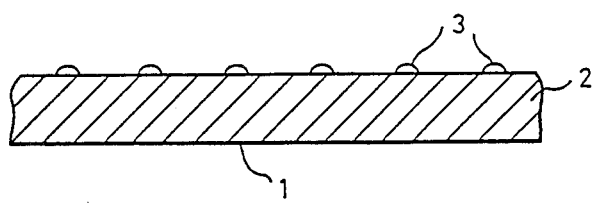
FIG. 4 is a sectional view on an enlarged scale of a portion of the material of FIG. 3.

FIG. 3 shows the pre-treatment sheet 1 manufactured in this example. The sheet 1 carries a cyanoacrylate based adhesive 3 on a polyvinyl chloride film 2. FIG. 4 is an enlarged sectional view of a part of the above sheet.

Manufacturing Example 3

A vinyl acetate emulsion based adhesive having the following composition was applied on a surface of a cellophane tape, in the form of strips (width: 30 μm, space: 3 mm), to obtain the pre-treatment tape of the present invention (adhesive density: 0.9%).

| Composition | Parts by weight |
| --- | --- |
| $H_2O$ | 1,050 |
| $H_2O_2$ (40%) | 3 |
| Polyvinyl alcohol | 52 |

-continued

| Composition | Parts by weight |
| --- | --- |
| Vinyl acetate monomer | 1,050 |
| Formic acid | 2.0 |

Figure 5:
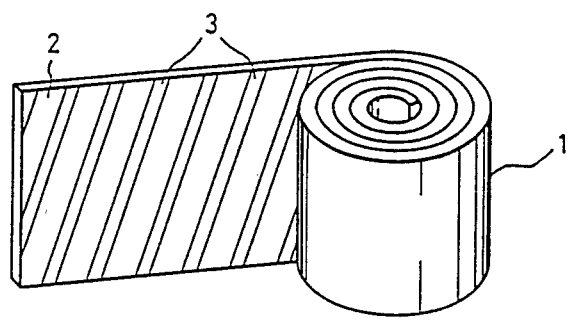
FIG. 5 is a plan view of another embodiment of the pre-treatment material according to the present invention.

FIG. 5 shows the tape 1 of this example carrying a vinyl acetate emulsion based adhesive 3 on a cellophane support 2.

Manufacturing Example 4

A capsular adhesive based on cyanoacrylate (Sumitomo 3M: Scotch-Grip Fastener Adhesive 2353) was scatteringly and uniformly applied on a surface of a celluloid plate (7 cm×8 cm×10 mm), at a density of 0.1%, to obtain the pre-treatment material of the present invention.

Figure 6:
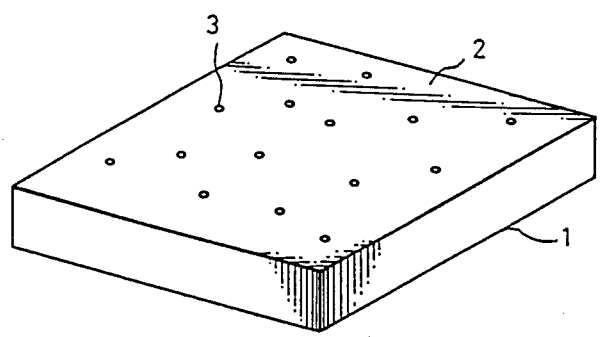
FIG. 6 is a plan view of still another embodiment of the pre-treatment material according to the present invention.

FIG. 6 shows the pre-treatment material 1 of this example. The material 1 carries microcapsules 3 on a celluloid support 2.

Manufacturing Example 5

Figure 7:
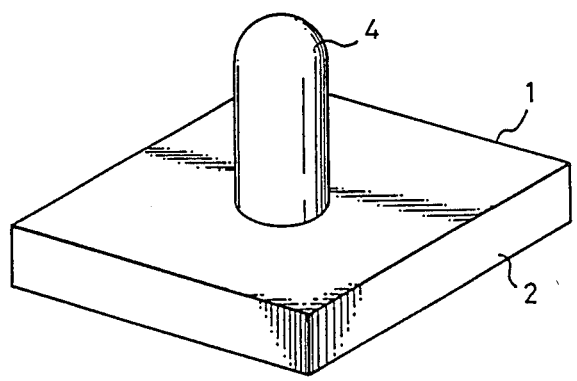
FIG. 7 is a plan view of yet another embodiment of the pre-treatment material according to the present invention.

As shown in FIG. 7, the pre-treatment material 1 was manufactured by applying the adhesive as in the Manufacturing Example 4 on the surface of the rigid polyvinyl chloride plate 2 (5 cm×10 cm×5 mm) opposite to the surface having the cylindrical handle 4.

Use Example 1

The pre-treatment material produced in the Manufacturing Example 1 according to the present invention was put on a facies lateralis brachii of a human and then peeled therefrom. Before and after the operation by the pre-treatment material of the present invention, the impedances were determined by applying a voltage at a frequency of 10 Hz, with a function generator (oscilloscope), and a reduction of resistance to one fifth due to the operation of the pre-treatment material of the present invention, was observed.

Use Examples 2-4

The same tests as in the Use Example 1 were performed, using the pre-treatment materials produced in the Manufacturing Examples 2-4 according to the present invention. The results are shown as follows:

| Use Example | Pre-treatment material used | Reduction in impedance |
| --- | --- | --- |
| | | (After operation/before operation) |
| 2 | Sheet of Manufacturing Example 2 | 1/10 |
| 3 | Tape of Manufacturing Example 3 | 1/7 |
| 4 | Plate of Manufacturing Example 4 | ⅛ |

In each of the Use Examples 2-4, irritation such as erythrochromia was not found on the skin.

INDUSTRIAL APPLICABILITY

The effect on the skin of the material for endermic administration pre-treatment according to the present invention resulted in a remarkable reduction of the physical and electrical resistances inherently exhibited by skin tissue against absorption of the medicament, without substantial irritation of the skin, thereby allowing a subsequent particularly efficient endermic administration to be carried out.

I claim:

1. In inontophoretic transdermal drug administration, the improved method which comprises pre-treating a portion of the skin to which the drug administration is to be made by pressing a substance capable of removing stratum corneum, and which is substantially uniformly distributed on a support in the form of small areas discontinuous to each other at a density of 0.001 to 5%, against a portion of the skin to which the drug administration is to be made, adhering said substance to the stratum corneum on said skin, and removing the substance together with the support from the skin so as to remove a portion of the stratum corneum and provide fine openings in the stratum corneum having reduced impedance and permitting enhanced iontophoretic transdermal drug administration.

2. The method according to claim 1, wherein said substance capable of removing stratum corneum is an adhesive substantially non-toxic to skin.

3. The method according to claim 2, wherein said adhesive is a pressure sensitive adhesive.

4. The method according to claim 3, wherein said pressure sensitive adhesive is a capsular adhesive.

5. The method according to claim 3, wherein said pressure sensitive adhesive is a natural adhesive, thermoplastic adhesive or synthetic rubber adhesive.

6. The method according to claim 1, wherein said small area is a circle having a diameter of about 10-300 μm.

7. The method according to claim 1, wherein said small area is a strip having a width of about 10-300 μm.

8. The method according to claim 1 having a density of 0.01 to 5%.

9. The method according to claim 1, wherein the support is a flexible sheet.

10. The method according to claim 1, wherein the support is a rigid plate.

11. The method according to claim 1, wherein the rigid plate has a handle on a surface opposite to a surface carrying the substance capable of removing stratum cornes.

* * * * *